United States Patent [19]
Redl et al.

[11] Patent Number: 5,139,527
[45] Date of Patent: Aug. 18, 1992

[54] BIOLOGIC ABSORBABLE IMPLANT MATERIAL FOR FILLING AND CLOSING SOFT TISSUE CAVITIES AND METHOD OF ITS PREPARATION

[75] Inventors: Heinz Redl; Günther Schlag; Nestor Pridun, all of Vienna, Austria

[73] Assignee: Immuno Aktiengesellschaft, Vienna, Austria

[21] Appl. No.: 563,804

[22] Filed: Aug. 6, 1990

Related U.S. Application Data

[63] Continuation of Ser. No. 283,841, Dec. 13, 1988, abandoned.

[30] Foreign Application Priority Data

Dec. 17, 1987 [AT] Austria ............................. 3337/87

[51] Int. Cl.⁵ ............................................. A61F 2/54
[52] U.S. Cl. ..................................................... 623/66
[58] Field of Search ..................... 623/16, 66, 11, 13

[56] References Cited

U.S. PATENT DOCUMENTS

| | | | |
|---|---|---|---|
| 4,120,649 | 10/1978 | Schechter | 8/94.11 |
| 4,172,128 | 10/1979 | Thiele et al. | 623/16 X |
| 4,277,238 | 7/1981 | Katagiri | 623/16 X |
| 4,347,234 | 8/1982 | Wahlig et al. | 623/16 X |
| 4,472,840 | 9/1984 | Jefferies | 623/16 |
| 4,620,327 | 11/1986 | Caplan et al. | 623/16 X |
| 4,627,853 | 12/1986 | Campbell et al. | 623/16 |
| 4,642,120 | 2/1987 | Nevo et al. | 623/16 |

FOREIGN PATENT DOCUMENTS

| | | |
|---|---|---|
| 0171176 | 2/1986 | European Pat. Off. |
| 0174737 | 3/1986 | European Pat. Off. |
| 961654 | 4/1957 | Fed. Rep. of Germany |
| 2854490 | 6/1980 | Fed. Rep. of Germany |

OTHER PUBLICATIONS

Current Research Review, Induced Osteogenesis-The Biological Principle and Clinical Applications. Journal of Surgical Research 37, 487–496 (1984).

*Primary Examiner*—David Isabella
*Assistant Examiner*—Gina M. Gualtieri
*Attorney, Agent, or Firm*—Burns, Doane, Swecker & Mathis

[57] ABSTRACT

There is disclosed a biologic absorbable implant material for filling and closing soft-tissue cavities and for replacing soft-tissue parts, and a method of its preparation. The implant material consists essentially of bone tissue of human or animal origin, is decalcified, and the original protein content of the osseous hard substance is unchanged. By cross-linking of these native proteins with a cross-linking agent, a high elasticity, a good stability and a marked memory-effect are attained. The method for the preparation of the implant material includes degreasing, decalcification and cross-linking of the available proteins and then drying and sterilizing of the material.

5 Claims, 1 Drawing Sheet

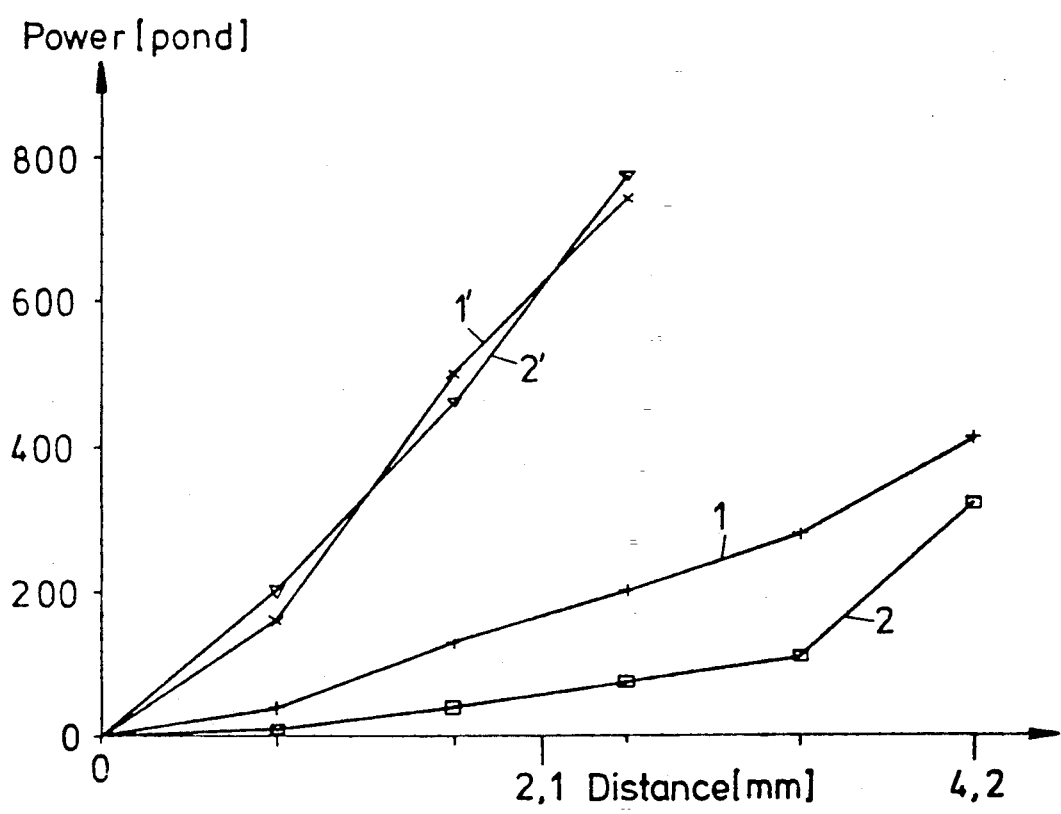

BIOLOGIC ABSORBABLE IMPLANT MATERIAL FOR FILLING AND CLOSING SOFT TISSUE CAVITIES AND METHOD OF ITS PREPARATION

This application is a continuation of application Ser. No. 283,841, filed Dec. 13, 1988, now abandoned.

The present invention relates to a biologic absorbable implant material for filling and closing soft-tissue cavities and for replacing soft-tissue parts, as well as to a method of its preparation.

In the field of orthopedics, implant materials for filling bone cavities are known, which are produced by partial deproteinisation and denaturation of the residual protein from spongiosa bone tissue (German Patent No. 961,654). This material, which is known as "Kieler spongiosa", basically has the same calcium content as native spongiosa. Consequently, it is hard and totally inelastic, thus it is unsuited for application in soft-tissue parts.

In bone surgery, a material produced from cortical bones, i.e., tubular bones, by decalcification is known (Journal of Surgical Research 37, 487–496 (1984)), which has an osteoinductive effect supposed to be due to its content of bone morphogenetic protein. On account of this osteoinductive property, its use outside of bones is contra-indicated.

In EP-A No. 0,171,176, a composition for repairing bone defects is described, which is prepared from bone collagen by decalcification and lyophilization, and which forms a gel upon reconstitution. On account of the desired osteoinductive effect of this material, care is taken that no cross-link formation of the collagen occurs during preparation.

Furthermore, a collagen-based bone substitute material is known from German Auslegeschrift No. 28 54 490. It is prepared from bones by removing the blood pigment and other water-soluble proteins, degreasing and eliminating the mineral portions by means of complexing agents or ion exchangers and finally freeze-drying. Upon reconstitution, the material is insufficiently elastic and not suited for application in soft tissue parts.

So far, only collagen fleeces have become known as coverage and implant materials for the application at or in soft tissue parts. However, such fleeces have no dimensional stability and no elasticity in the moist state; they are suited for firm bonding to mobile tissue, e.g., to the lung, to a limited extent only. Synthetic materials, such as acrylates, which likewise have been proposed, have still other disadvantages, among which massive stimulus caused by a foreign body, encapsulation, insufficient healing and the possible release of toxic decomposition and side products are particularly emphasized.

Further known prior art prosthetic implant materials are produced from body tissues by treatment with protein cross-linking agents. Such materials are used in order to increase the stability of certain organs, e.g., of cardiac valves or vascular prostheses. Such implants are described, for instance, in EP-B No. 0,174,737 and in U.S. Pat. No. 4,120,649.

The invention has as its object to provide a well tolerated implant material that may be used to close tissue cavities, on the one hand, and to substitute certain tissue parts, on the other hand, and which does not have the disadvantageous properties of the known products, which limit their therapeutic utilization.

After lung resections and also after other diseases of the lung, bronchopleural fistulas may occur. These are septic openings or cavities forming between the bronchial tree and the pleura and are filled with secretions and pus. They are constantly passed by air and secretions during breathing and coughing. Their sizes range from a few millimeters to several centimeters in diameter. Therefore, it is a still unsolved problem in thorax surgery how to seal such bronchial fistulas and how to enhance curing of the same, in particular, if the introduction of the implant is to be effected by way of endoscopy, which is the quickest and mildest way. Special demands are required of an implant material to be introduced and fixed endoscopically. On the one hand, mechanical spreading must be feasible, on the other hand, introduction through the bronchial tree to the fistula must be possible.

The implant must be deformable and compressible. It must be able to reassume its original shape in the presence of moisture, i.e., it must have a high memory effect. In addition, the material must offer a considerable strength, yet remain absorbable, because germs may adhere to non-absorbable materials, thus causing abscesses and new fistulas again and again. Besides, according to a further aspect of the invention, it is possible to obtain a gas- and liquid-tight closure immediately upon introduction of the implant. Finally, it is possible to incorporate into the material bactericidal and/or other pharmaceutical substances in order to stimulate wound healing.

The invention which achieves these objects with a biologic absorbable implant material for filling and closing soft tissue cavities and for replacing soft tissue parts consists of the implant material consisting essentially of bone tissue of human or animal origin molded into shaped products, which is decalcified, whose native proteins are cross-linked with a protein cross-linking agent in order to avoid osteoinductive activity, the shaped products exhibiting a high elasticity at a low hysteresis between loaded and unloaded conditions.

Thus, according to the invention, the initial protein content of the decalcified osseous hard substance remains almost unchanged and the high elasticity and stability are brought about by the cross-link formation of the native proteins.

The shaped products formed of bone tissue may, for instance, have block, conical or spherical shapes.

For the replacement of tubular soft parts, such as trachea pieces, the implant material, preferably, is produced from cortical bone parts.

To fill and close tissue cavities, the implant material may be produced from spongiosa bone parts and may have spongy consistency, the pore volume of the material being 55 to 95%. The material is compressible in the dry state; however, it reassumes its original shape in the presence of moisture, which means that it has a marked memory effect.

Decalcification is continued until the residual content of calcium amounts to 80 mMol/g wet weight at the most.

According to a preferred embodiment, the implant material may contain a tissue adhesive based on fibrinogen or collagen.

The invention, furthermore, relates to a method of preparing the implant material, which is characterized in that native protein-containing bone material is decalcified by a decalcifying agent, is washed free from the decalcification agent, is then treated with a protein cross-linking agent, is repeatedly washed to remove the protein cross-linking agent, if desired, is combined with pharmaceutical solutions, such as tissue adhesive solutions based on fibrinogen or collagen, and finally is dried and sterilized.

As for the cross-linking agents, aldehydes, in particular glutaraldehyde, polyepoxide compounds, isodicyanate derivatives or carbodiimides may be used.

The bone material, suitably, may be degreased by means of an organic solvent, such as chloroform-methanol, before or after decalcification.

There may also be provided to treat the bone material, before or after protein cross-linking, agents, e.g., detergents or enzymes that reduce the content of undesired antigens.

The implant material according to the invention and the method of its preparation may be modified in various aspects to impart additional pharmaceutical effects and properties. Thus, when using a detergent, e.g., octylphenoxy-polyethoxyethanol triton X-100 in a one-percent concentration, in the washing solutions, it is not only possible to reduce the content of undesired antigens, but the danger of a subsequent calcification of the implant may be lowered, too. Moreover, a low content (about 0.5M) of ethylenediaminetetraacid sodium may be provided in the washing solutions, whereby decalcification is improved.

The intermediate treatment of the implant material with a buffer solution containing enzymatically effective substances, for instance, ficin and/or neuraiminidase, may be provided, which likewise reduces the antigen content in the finished product.

In order to make sure that the finished product will not contain any traces of glutaraldehyde, the material may be rinsed with a glycine or lysine solution (content about 5 mg/ml) after the cross-linking treatment.

If the implant material according to the invention has been produced from spongiosa, it is suitable if the implant material is compressed, approximately to half its volume, prior to being filled into final containers.

A special field of application of the material according to the invention is the substitution for tubular tissue parts, such as trachea parts. As the starting material for such an implant, femur bones are used, which are tubularly reduced to a wall thickness of about 2 mm by mechanical surface abrasion on a lathe, before being subjected to the combined treatment by decalcification and protein cross-linking according to the invention.

The end product according to the invention, if destined to fill tissue cavities, suitably is brought into block shape.

The material may be sterilized by gamma rays and may be stored in containers, which, for instance, contain a 70% ethanol solution. The blocks are rinsed with a Ringer solution prior to being applied into patients.

It is also possible to store the blocks in a dry state after sterilization with gamma rays, wherein, according to a particularly preferred embodiment of the invention, the blocks are soaked with a fibrin sealant under sterile conditions and subsequently are lyophilized in the final container.

Naturally, the product according to the invention, in addition to the block or tubular shape already described, may be made available also in disk or sheet form.

The method according to the invention and the product produced thereby will be explained in more detail in the following example.

1 kg of spongiosa bone material from the calf was obtained by cutting the head of a femur into cubes. Only the spongiosa bones parts were used in the preparation of the product of the invention according to this example.

These spongiosa cubes were rinsed with hot water (50° C.) and subsequently were decalcified at room temperature in 0.6N hydrochloric acid (10 l) under continuous motion and by repeatedly changing, pressing and washing the spongiosa blocks (24 to 72 hours). Subsequently, the blocks were washed free of acid and incubated with 1% glutaraldehyde in a 0.05M phosphate buffer solution (1 l) at a pH of 7.4 at room temperature for one hour so as to effect cross-linking.

By washing with a sterile washing solution and pressing of the spongiosa for at least five times, the residual glutaraldehyde was removed from the spongiosa. The blocks were freeze-dried, filled into final containers and sterilized within the same by means of 2.5 Mrad gamma rays.

The thus produced implant material in block form was inserted into patients as a fistula closure by way of endoscopy: The patient was intubated with a rigid bronchoscope and respiration in the open system was performed by means of jet ventilation. After inspection of the fistula, a suitable spongiosa piece was cut and compressed so as to be able to be guided through the bronchus with the bronchoscope. The implant was placed into the fistula by biopsy forceps, where it got moistened upon contact with the bronchial wall, expanding very rapidly and spreading. Immediately upon setting of the implant, 1 to 2 ml of a fibrin sealant were dropped about the implant by a three-lumen spraying catheter, the implant, thus, swelling further and bonding with the bronchial wall. An immediate air-tight closure of the fistula was obtained.

The implant material according to the invention does not exert any osteoinductive effect, which can be proved by measuring alkaline phosphatase and by histologic investigations. Consequently, the material can safely be used for application in soft tissue regions.

The implant material produced according to the invention has excellent elasticity properties. For the purpose of comparison with known preparations, spongiosa blocks having an edge length of 1.5 cm were produced, once without treatment with a protein cross-linking agent and once with the treatment according to the invention by combined decalcification and protein cross-linking as described in the above embodiment. The blocks were dried and then were moistened with a 0.9% NaCl solution. All the blocks were checked in a loading apparatus (transducer 0–1000 pond (gram-force, fors) at a loading speed of 1 cm/min), with load and relief curves resulting, which are illustrated in the drawing.

The load curve and the relief curve (power—distance) distance) of the spongiosa blocks that have not been subjected to cross-linking are denoted by 1 and 2; 1' and 2' represent the respective curves of the preparations according to the invention. It is apparent that, with the prior art preparations, which have not been cross-linked, a relatively low strength and an intense hysteresis occur, whereas the spongiosa blocks according to the invention do not develop any signs of hysteresis and exhibit high strength values.

The tissue tolerance of spongiosa blocks according to the invention, having the dimensions of 0.5×0.5×1 cm and produced according to the exemplary embodiment, was tested in rat experiments. The blocks were implanted subcutaneously into the backs of the rats, were removed at various time intervals, were fixed and processed histologically.

It appeared that noncross-linked spongiosa blocks showed more intensive inflammatory reactions, more foreign-body giant cells, more fibrosis and the tendency to absorption after 2 weeks, there were clear signs of disintegration occurring after 4 weeks. In contrast, no such side effects could be observed with the samples treated according to the invention.

What we claim is:

1. A bioabsorbable soft tissue implant material for filling and closing soft-tissue cavities said implant material consists essentially of decalcified spongiosa bone tissue of human or animal origin prepared from spongiosa bone parts, having spongy consistency, and molded into shaped products, wherein said bone tissue has its native proteins cross-linked by a protein cross-linking agent so as to avoid osteoinductive effects, the pore volume of the material being 55 to 95%, said shaped products are elastic in the moistened condition and have a low hysteresis between loaded and unloaded conditions.

2. An implant material as set forth in claim 1, in combination with pharmaceutically active substances.

3. An implant material as set forth in claim 1, which is compressible in the dry state, yet is capable of reassuming its original shape in the presence of moisture, thus exhibiting a marked memory effect.

4. An implant material as set forth in claim 1, wherein the maximum residual calcium content is 80 mMol/g wet weight.

5. An implant material as set forth in claim 1, in combination with a tissue adhesive based on fibrinogen or collagen.

* * * * *